United States Patent
Sweeney et al.

(10) Patent No.: US 7,425,210 B2
(45) Date of Patent: Sep. 16, 2008

(54) DRUG DELIVERY SYSTEM FOR IMPLANTABLE MEDICAL DEVICE

(75) Inventors: Robert J. Sweeney, Woodbury, MN (US); Avram Scheiner, Vadnais Heights, MN (US); Ronald W. Heil, Jr., Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 834 days.

(21) Appl. No.: 10/743,507

(22) Filed: Dec. 22, 2003

(65) Prior Publication Data

US 2004/0138648 A1    Jul. 15, 2004

Related U.S. Application Data

(62) Division of application No. 09/740,129, filed on Dec. 18, 2000, now Pat. No. 6,689,117.

(51) Int. Cl.
  *A61K 9/22* (2006.01)
(52) U.S. Cl. .................................. 604/891.1
(58) Field of Classification Search ............. 604/24, 604/25, 26, 891.1, 890.1, 65–67, 503; 261/142, 261/130, 96, 105; 96/371; 128/DIG. 12, 128/DIG. 13; 600/547; 607/32, 30, 57, 60, 607/3–6
See application file for complete search history.

(56) References Cited

U.S. PATENT DOCUMENTS

| | | | |
|---|---|---|---|
| 3,692,027 A | 9/1972 | Elinwood, Jr. | 128/260 |
| 4,003,379 A | 1/1977 | Ellinwood, Jr. | 128/260 |
| 4,146,029 A | 3/1979 | Ellinwood, Jr. | 128/260 |
| 4,202,340 A | 5/1980 | Langer et al. | |
| 4,271,192 A | 6/1981 | Wurtman et al. | |
| 4,281,664 A | 8/1981 | Duggan | 128/696 |
| 4,299,220 A | 11/1981 | Dorman | 128/260 |
| 4,470,987 A | 9/1984 | Wurtman et al. | |
| 4,544,371 A | 10/1985 | Dormandy, Jr. et al. | 604/891 |
| 4,556,063 A | 12/1985 | Thompson et al. | 128/419 PT |

(Continued)

FOREIGN PATENT DOCUMENTS

EP    0054138    10/1981

(Continued)

OTHER PUBLICATIONS

Arnaud, Claire, et al., "iNOS is a mediator of the heat stress-induced preconditioning against myocardial infarction in vivo in the rat", *Cardiovascular Research*, 58, (2003),118-125.

(Continued)

*Primary Examiner*—Manuel A Mendez
(74) *Attorney, Agent, or Firm*—Schwegman, Lundberg & Woessner, P.A.

(57) ABSTRACT

A drug delivery system and method in which an implantable medical device communicates with and controls an external drug delivery device with low energy potential signals. The implantable device generates potential signals modulated with digitally encoded command information by operating a current source to cause corresponding electrical potentials that can be sensed at the skin surface by the external drug delivery device. The drug delivery device then demodulates the sensed potentials and decodes the digital data to extract command information therefrom to deliver a drug accordingly.

10 Claims, 3 Drawing Sheets

U.S. PATENT DOCUMENTS

| | | | |
|---|---|---|---|
| 4,559,946 A | 12/1985 | Mower | |
| 4,561,443 A | 12/1985 | Hogrefe et al. | |
| 4,651,716 A | 3/1987 | Forester et al. | |
| 4,674,518 A | 6/1987 | Salo | |
| 4,686,987 A | 8/1987 | Salo et al. ............ 128/419 PG |
| 4,693,253 A | 9/1987 | Adams | |
| 4,787,389 A | 11/1988 | Tarjan | |
| 4,790,317 A | 12/1988 | Davies | |
| 4,871,351 A | 10/1989 | Feingold ..................... 604/66 |
| 4,880,005 A | 11/1989 | Pless et al. | |
| 4,897,987 A | 2/1990 | Spalla ....................... 56/16.7 |
| 4,904,472 A | 2/1990 | Belardinelli et al. | |
| 4,924,875 A | 5/1990 | Chamoun | |
| 4,930,075 A | 5/1990 | Kortas | |
| 4,940,054 A | 7/1990 | Grevis et al. | |
| 4,944,299 A | 7/1990 | Silvian ................ 128/419 PG |
| 4,949,719 A | 8/1990 | Pless et al. | |
| 4,980,379 A | 12/1990 | Belardinelli et al. | |
| 4,987,897 A | 1/1991 | Funke ................. 128/419 PG |
| 5,002,052 A | 3/1991 | Haluska | |
| 5,014,698 A | 5/1991 | Cohen | |
| 5,040,533 A | 8/1991 | Fearnot ................ 128/419 PG |
| 5,041,107 A | 8/1991 | Heil, Jr. .................. 604/891.1 |
| 5,042,497 A | 8/1991 | Shapland .................... 600/509 |
| 5,058,581 A | 10/1991 | Silvian ................ 128/419 PG |
| 5,087,243 A | 2/1992 | Avitall ........................ 604/20 |
| 5,113,869 A | 5/1992 | Nappholz et al. | |
| 5,127,404 A | 7/1992 | Wyborny et al. ......... 128/419 P |
| 5,135,004 A | 8/1992 | Adams et al. | |
| 5,137,019 A | 8/1992 | Pederson et al. | |
| 5,179,945 A | 1/1993 | Van Hofwegen et al. | |
| 5,179,946 A | 1/1993 | Weiss | |
| 5,184,614 A | 2/1993 | Collins et al. | |
| 5,188,105 A | 2/1993 | Keimel | |
| 5,190,035 A | 3/1993 | Salo et al. ................... 128/419 |
| 5,193,535 A | 3/1993 | Bardy et al. | |
| 5,199,428 A | 4/1993 | Obel et al. | |
| 5,215,083 A | 6/1993 | Drane et al. | |
| 5,220,917 A | 6/1993 | Cammilli et al. ........ 128/419 D |
| 5,269,301 A * | 12/1993 | Cohen ........................... 607/6 |
| 5,282,836 A | 2/1994 | Kreyenhagen et al. | |
| 5,284,136 A | 2/1994 | Hauck et al. ................... 607/24 |
| 5,292,338 A | 3/1994 | Bardy | |
| 5,301,677 A | 4/1994 | Hsung | |
| 5,305,745 A | 4/1994 | Zacouto ..................... 128/637 |
| 5,325,856 A | 7/1994 | Nitzsche et al. | |
| 5,334,222 A | 8/1994 | Salo et al. | |
| 5,342,408 A | 8/1994 | deCoriolis et al. ............. 607/32 |
| 5,346,506 A | 9/1994 | Mower et al. | |
| 5,350,406 A | 9/1994 | Nitzsche et al. | |
| 5,353,800 A | 10/1994 | Pohndorf et al. ............. 128/673 |
| 5,354,317 A | 10/1994 | Alt | |
| 5,366,485 A | 11/1994 | Kroll et al. | |
| 5,368,028 A | 11/1994 | Palti ........................... 128/635 |
| 5,379,776 A | 1/1995 | Murphy et al. | |
| 5,391,190 A | 2/1995 | Pederson et al. | |
| 5,404,877 A | 4/1995 | Nolan et al. ................ 128/671 |
| 5,405,362 A | 4/1995 | Kramer et al. | |
| 5,411,474 A * | 5/1995 | Ott et al. ....................... 604/26 |
| 5,416,695 A | 5/1995 | Stutman et al. ........ 364/413.02 |
| 5,417,717 A | 5/1995 | Salo et al. | |
| 5,431,682 A | 7/1995 | Hedberg | |
| 5,439,483 A | 8/1995 | Duong-Van | |
| 5,441,525 A | 8/1995 | Shelton et al. | |
| 5,456,692 A | 10/1995 | Smith, Jr. et al. ............. 607/31 |
| 5,458,619 A | 10/1995 | Olson | |
| 5,460,605 A | 10/1995 | Tuttle et al. ................... 604/67 |
| 5,464,434 A | 11/1995 | Alt | |
| 5,476,503 A | 12/1995 | Yang | |
| 5,487,752 A | 1/1996 | Salo et al. | |
| 5,489,293 A | 2/1996 | Pless et al. | |
| 5,496,360 A | 3/1996 | Hoffmann et al. ............ 607/120 |
| 5,499,971 A | 3/1996 | Shapland et al. ............... 604/53 |
| 5,500,008 A | 3/1996 | Fain | |
| 5,501,701 A | 3/1996 | Markowitz et al. | |
| 5,522,853 A | 6/1996 | Kroll | |
| 5,531,768 A | 7/1996 | Alferness | |
| 5,540,723 A | 7/1996 | Ideker et al. | |
| 5,540,728 A | 7/1996 | Shelton et al. | |
| 5,545,186 A | 8/1996 | Olson et al. | |
| 5,545,205 A | 8/1996 | Schulte et al. | |
| 5,551,953 A | 9/1996 | Lattin et al. ................... 604/20 |
| 5,556,421 A | 9/1996 | Prutchi et al. .................. 607/36 |
| 5,562,711 A | 10/1996 | Yerich et al. | |
| 5,562,713 A | 10/1996 | Silvian ........................ 607/32 |
| 5,579,876 A | 12/1996 | Adrian et al. ........... 188/322.17 |
| 5,584,868 A | 12/1996 | Salo et al. | |
| 5,586,556 A | 12/1996 | Spivey et al. ................ 128/697 |
| 5,591,215 A | 1/1997 | Greenhut et al. | |
| 5,603,331 A | 2/1997 | Heemels et al. | |
| 5,607,418 A | 3/1997 | Arzbaecher ................ 604/891.1 |
| 5,607,463 A | 3/1997 | Schwartz et al. | |
| 5,632,766 A | 5/1997 | Hsu | |
| 5,634,899 A | 6/1997 | Shapland et al. ............... 604/51 |
| 5,662,689 A | 9/1997 | Elsberry et al. ................. 607/5 |
| 5,676,686 A | 10/1997 | Jensen et al. | |
| 5,683,424 A | 11/1997 | Brown et al. | |
| 5,690,682 A | 11/1997 | Buscemi et al. ................. 607/3 |
| 5,693,075 A | 12/1997 | Plicchi et al. .................. 607/17 |
| 5,703,125 A | 12/1997 | Bovy et al. ................... 128/637 |
| 5,706,829 A | 1/1998 | Kadri | |
| 5,709,215 A | 1/1998 | Perttu et al. | |
| 5,720,770 A | 2/1998 | Nappholz et al. .............. 607/30 |
| 5,725,561 A | 3/1998 | Stroebel et al. | |
| 5,725,562 A | 3/1998 | Sheldon | |
| 5,730,125 A | 3/1998 | Prutchi et al. ................ 128/637 |
| 5,730,141 A | 3/1998 | Fain et al. | |
| RE35,779 E | 4/1998 | Alferness et al. | |
| 5,741,214 A * | 4/1998 | Ouchi et al. .................. 600/374 |
| 5,749,900 A | 5/1998 | Schroeppel et al. | |
| 5,772,604 A | 6/1998 | Langberg et al. | |
| 5,782,876 A | 7/1998 | Flammang | |
| 5,782,879 A | 7/1998 | Rosborough et al. | |
| 5,797,967 A | 8/1998 | KenKnight | |
| 5,800,464 A | 9/1998 | Kieval | |
| 5,800,498 A | 9/1998 | Obino et al. ................. 607/123 |
| 5,814,081 A | 9/1998 | Ayers et al. | |
| 5,814,089 A | 9/1998 | Stokes et al. | |
| 5,817,131 A | 10/1998 | Elsberry et al. ................. 607/5 |
| 5,833,603 A | 11/1998 | Kovacs et al. ................ 600/317 |
| 5,836,935 A | 11/1998 | Ashton et al. ............. 604/891.1 |
| 5,874,420 A | 2/1999 | Pelleg | |
| 5,876,353 A | 3/1999 | Riff | |
| 5,879,295 A | 3/1999 | Li et al. | |
| 5,893,881 A | 4/1999 | Elsberry et al. ................. 607/5 |
| 5,899,928 A | 5/1999 | Sholder et al. ................. 607/27 |
| 5,906,633 A | 5/1999 | Mouchawar et al. | |
| 5,913,879 A | 6/1999 | Ferek-Petric et al. | |
| 5,916,239 A | 6/1999 | Geddes et al. | |
| 5,919,210 A | 7/1999 | Lurie et al. | |
| 5,925,066 A | 7/1999 | Kroll et al. ..................... 607/3 |
| 5,949,659 A | 9/1999 | Lesche ......................... 363/16 |
| 5,954,761 A | 9/1999 | Machek et al. | |
| 5,957,861 A | 9/1999 | Combs et al. | |
| 5,957,957 A | 9/1999 | Sheldon | |
| 5,967,986 A | 10/1999 | Cimochowski et al. ...... 600/454 |
| 5,968,079 A | 10/1999 | Warman et al. | |
| 5,978,705 A | 11/1999 | KenKnight et al. | |
| 5,991,660 A | 11/1999 | Goyal | |
| 5,991,668 A | 11/1999 | Leinders et al. ............. 607/125 |
| 6,010,118 A * | 1/2000 | Milewicz .................... 261/142 |
| 6,016,447 A | 1/2000 | Juran et al. .................... 607/27 |
| 6,016,448 A | 1/2000 | Busacker et al. .............. 607/29 |
| 6,021,350 A | 2/2000 | Mathson | |

| | | |
|---|---|---|
| 6,022,322 A | 2/2000 | Prutchi |
| 6,035,233 A | 3/2000 | Schroeppel et al. |
| 6,044,297 A | 3/2000 | Sheldon et al. |
| 6,049,735 A | 4/2000 | Hartley et al. |
| 6,052,614 A * | 4/2000 | Morris et al. ............... 600/509 |
| 6,076,015 A | 6/2000 | Hartley et al. |
| 6,078,834 A | 6/2000 | Lurie et al. |
| 6,104,949 A | 8/2000 | Pitts Crick et al. |
| 6,112,117 A | 8/2000 | KenKnight et al. |
| 6,115,636 A | 9/2000 | Ryan ........................ 607/60 |
| 6,128,526 A | 10/2000 | Stadler et al. |
| 6,140,740 A | 10/2000 | Porat et al. .................. 310/322 |
| 6,141,588 A | 10/2000 | Cox et al. |
| 6,154,672 A | 11/2000 | Pendekanti et al. |
| 6,154,675 A | 11/2000 | Juran et al. .................... 607/29 |
| 6,155,267 A | 12/2000 | Nelson |
| 6,161,042 A | 12/2000 | Hartley et al. |
| 6,168,801 B1 | 1/2001 | Heil, Jr. et al. ............... 424/426 |
| 6,198,394 B1 | 3/2001 | Jacobsen et al. ......... 340/573.1 |
| 6,200,265 B1 | 3/2001 | Walsh et al. ................. 600/300 |
| 6,203,495 B1 | 3/2001 | Bardy |
| 6,206,914 B1 | 3/2001 | Soykan et al. ............... 623/1.42 |
| 6,212,434 B1 | 4/2001 | Scheiner et al. |
| 6,213,942 B1 | 4/2001 | Flach et al. ................. 600/300 |
| 6,221,011 B1 | 4/2001 | Bardy |
| 6,231,516 B1 | 5/2001 | Keilman et al. ............. 600/485 |
| 6,237,398 B1 | 5/2001 | Porat et al. .................. 73/54.09 |
| 6,251,125 B1 | 6/2001 | KenKnight et al. |
| 6,254,573 B1 | 7/2001 | Haim et al. .................. 604/157 |
| 6,256,233 B1 | 7/2001 | Glass |
| 6,256,541 B1 | 7/2001 | Heil et al. |
| 6,261,230 B1 | 7/2001 | Bardy |
| 6,266,554 B1 | 7/2001 | Hsu et al. |
| 6,270,457 B1 | 8/2001 | Bardy |
| 6,272,377 B1 | 8/2001 | Sweeney et al. |
| 6,277,072 B1 | 8/2001 | Bardy |
| 6,277,078 B1 | 8/2001 | Porat et al. .................. 600/486 |
| 6,278,894 B1 | 8/2001 | Salo et al. |
| 6,280,380 B1 | 8/2001 | Bardy |
| 6,285,898 B1 | 9/2001 | Ben-Haim |
| 6,285,909 B1 | 9/2001 | Sweeney et al. |
| 6,298,267 B1 | 10/2001 | Rosborough et al. |
| 6,298,269 B1 | 10/2001 | Sweeney |
| 6,298,272 B1 | 10/2001 | Peterfeso et al. ............. 607/120 |
| 6,309,370 B1 | 10/2001 | Haim et al. .................... 604/66 |
| 6,312,378 B1 | 11/2001 | Bardy |
| 6,317,615 B1 | 11/2001 | KenKnight et al. |
| 6,317,631 B1 | 11/2001 | Ben-Haim et al. |
| 6,321,122 B1 | 11/2001 | Scheiner et al. |
| 6,331,160 B1 | 12/2001 | Bardy |
| 6,336,903 B1 | 1/2002 | Bardy |
| 6,358,202 B1 | 3/2002 | Arent ........................ 600/300 |
| 6,358,203 B2 | 3/2002 | Bardy |
| 6,361,522 B1 | 3/2002 | Scheiner et al. ............... 604/67 |
| 6,361,780 B1 | 3/2002 | Ley et al. .................... 424/400 |
| 6,363,281 B1 | 3/2002 | Zhu et al. |
| 6,368,284 B1 | 4/2002 | Bardy |
| 6,370,424 B1 | 4/2002 | Prutchi |
| 6,398,728 B1 | 6/2002 | Bardy |
| 6,400,982 B2 | 6/2002 | Sweeney et al. |
| 6,411,840 B1 | 6/2002 | Bardy |
| 6,411,844 B1 | 6/2002 | Kroll et al. |
| 6,415,183 B1 | 7/2002 | Scheiner et al. |
| 6,424,847 B1 | 7/2002 | Mastrototaro et al. ....... 600/316 |
| 6,438,419 B1 | 8/2002 | Callaway et al. |
| 6,440,066 B1 | 8/2002 | Bardy |
| 6,442,413 B1 | 8/2002 | Silver |
| 6,443,949 B2 | 9/2002 | Altman ........................ 606/41 |
| 6,453,195 B1 | 9/2002 | Thompson .................... 607/3 |
| 6,459,917 B1 | 10/2002 | Gowda et al. ............... 600/345 |
| 6,459,929 B1 | 10/2002 | Hopper et al. |
| 6,468,263 B1 | 10/2002 | Fischell et al. |
| 6,473,640 B1 | 10/2002 | Erlebacher |
| 6,478,737 B2 | 11/2002 | Bardy |
| 6,488,679 B1 * | 12/2002 | Swanson et al. ............... 606/40 |
| 6,501,983 B1 | 12/2002 | Natarajan et al. ........... 600/517 |
| 6,511,477 B2 | 1/2003 | Altman et al. ................. 606/41 |
| 6,518,245 B1 | 2/2003 | Anderson et al. ............. 514/14 |
| 6,519,488 B2 | 2/2003 | KenKnight et al. |
| 6,539,256 B1 | 3/2003 | KenKnight et al. |
| 6,604,000 B2 | 8/2003 | Lu |
| 6,628,985 B2 | 9/2003 | Sweeney et al. |
| 6,689,117 B2 | 2/2004 | Sweeney et al. |
| 2001/0000802 A1 | 5/2001 | Soykan et al. ............... 623/1.13 |
| 2002/0026228 A1 | 2/2002 | Schauerte |
| 2002/0031827 A1 | 3/2002 | Kanno et al. |
| 2002/0099328 A1 | 7/2002 | Scheiner et al. |
| 2002/0124855 A1 | 9/2002 | Chachques |
| 2003/0004403 A1 | 1/2003 | Drinan et al. ............... 600/301 |
| 2003/0060854 A1 | 3/2003 | Zhu |
| 2003/0069606 A1 | 4/2003 | Girouard et al. |
| 2003/0153952 A1 | 8/2003 | Auricchio et al. |
| 2003/0158584 A1 | 8/2003 | Cates et al. |
| 2003/0208240 A1 | 11/2003 | Pastore et al. |
| 2003/0233132 A1 | 12/2003 | Pastore et al. |
| 2004/0002739 A1 | 1/2004 | Cates et al. |
| 2004/0059391 A1 | 3/2004 | Sweeney et al. |
| 2004/0073262 A1 | 4/2004 | Lovett |
| 2004/0093034 A1 | 5/2004 | Girouard et al. |
| 2005/0043675 A1 | 2/2005 | Pastore et al. |
| 2005/0137626 A1 | 6/2005 | Pastore et al. |

FOREIGN PATENT DOCUMENTS

| | | |
|---|---|---|
| EP | 0347708 A1 | 12/1989 |
| EP | 0467695 A2 | 1/1992 |
| EP | 0545628 A2 | 6/1993 |
| EP | 0550343 A1 | 7/1993 |
| EP | 0550344 A1 | 7/1993 |
| EP | 0620420 A1 | 10/1994 |
| EP | 0674916 A2 | 10/1995 |
| EP | 1050265 | 11/2000 |
| WO | WO-93/20888 A1 | 10/1993 |
| WO | WO-96/32984 A1 | 10/1996 |
| WO | WO-97/06854 A1 | 2/1997 |
| WO | WO-97/33513 | 3/1997 |
| WO | WO-97/25098 A1 | 7/1997 |
| WO | WO-98/34537 A1 | 8/1998 |
| WO | WO-00/04947 A2 | 2/2000 |
| WO | WO-00/07497 A1 | 2/2000 |
| WO | WO-01/08748 A1 | 2/2001 |
| WO | WO-01/30436 A2 | 5/2001 |

OTHER PUBLICATIONS

Brunner, Friedrich, et al., "Attenuation of myocardial ischemia/reperfusion injury in mice with myocyte-specific overexpression of endothelial nitric oxide synthase", *CArdiovascular Research*, 57, (2003),55-62.

Ferdinandy, Peter, et al., "Nitric oxide, superoxide, and peroxynitrite in myocardial ischaemia-reperfusion injury and preconditioning", *British Journal of Pharmacology*, vol. 138, No. 4, (2003),532-543.

Flogel, Ulrich, et al., "Myoglobin: A scanvenger of bioactive NO", *PNAS*, vol. 98, No. 2, (Jan. 16, 2001),735-740.

Gewaltig, Michael T., et al., "Vasoprotection ny nitric oxide: mechanisms and therapeutic potential", *Cardiovascular Research*, 55, (Feb. 14, 2002),250-260.

Li, Qianghong, et al., "Gene Therapy With Inducible Nitric Oxide Synthase Protects Against Myocardial Infarction via a Cyclooxygenase-2-Dependent Mechanism", *Circulation Research*, 92, (2003),741-748.

Ostadal, Petr, et al., "The effect of early treatment by cerivastatin on the serum level of C-reactive protein, interleukin-6, and interleukin-8 in patients with unstable angina and non-Q-wave myocardial infarction", *Molecular and Cellular Biochemistry*, 246, (2003),45-50.

Paolocci, Nazareno, et al., "Positive inotropic and lusitropic effects of HNO-NO- in failing hearts: Independence from beta-adrenergic signaling", PNAS, vol. 100, No. 9, (Apr. 29, 2003),5537-5542.

Paolocci, N., et al., "Positive inotropic and lusitropic effects of HNO/NO- in failing hearts: Independence from beta-adrenergic signaling", *Proc. Natl. Acad. Sci. USA*, 100(9), 2003,4978-80.

Salloum, Fadi, et al., "Sildenafil Induces Delayed Preconditioning Through Inducible Nitric Oxide Synthase-Dependent Pathway in Mouse Heart", *Circulation Research*, 92, (Apr. 4, 2003), 595-597.

Suematsu, Yoshihiro, et al., "L-Arginine given after ischaemic pre-conditioning can enhance cardioprotection in isolated rat hearts", *European Journal of Cardio-thoracic Surgery*, 19, (2001),873-879.

Woldbaek, Per R., et al., "Increased cardiac IL-18 mRNA, pro-IL-18 and plasma IL-18 after myocardial infarction in the mouse; a potential role in cardiac dysfunction", *Cardiovascular Research*, 59, (2003),122-131.

Wolfrun, Sebastian, et al., "Acute Reduction of Myocardial Infarct Size By a Hydroxymethyl Glutaryl Coenzyme A Reductase Inhibitor is Mediated By Endothelial Nitric Oxide Synthase", *J. Cardiovas Pharmacol*, vol. 41, No. 3, (Mar. 2003),474-480.

Wunderlich, Carsten, et al., "Acute Inhibition of Myoglobin Impairs Contractility and Energy State of iNOS-Overexpressing Hearts", *Circulation Research*, 92, (2003),1352-1358.

* cited by examiner

DRUG DELIVERY SYSTEM FOR IMPLANTABLE MEDICAL DEVICE

CROSS-REFERENCE TO RELATED APPLICATION(S)

This application is a division of U.S. patent application Ser. No. 09/740,129, filed on Dec. 18, 2000, now issued as U.S. Pat. No. 6,689,117, the specification of which is incorporated herein by reference.

FIELD OF THE INVENTION

This invention pertains to implantable medical devices such as cardiac pacemakers and implantable cardioverter/defibrillators. In particular, the invention relates to a system and method enabling an implantable medical device to communicate with and control an external drug delivery device.

BACKGROUND

Implantable medical devices are commonplace today, particularly for treating cardiac dysfunction. Cardiac pacemakers, for example, are implantable medical devices that replace or supplement a heart's compromised ability to pace itself (i.e., bradycardia) due to chronotropic incompetence or a conduction system defect by delivering electrical pacing pulses to the heart. Implantable cardioverter/defibrillators (ICD's) are devices that deliver electrical energy to the heart in order to reverse excessively rapid heart rates (tachycardia) including life threatening cardiac arrhythmias such as ventricular fibrillation. Since some patients have conditions that necessitate pacing and also render them vulnerable to life-threatening arrhythmias, implantable cardiac devices have been developed that combine both functions in a single device.

Most pacemakers today are operated in some sort of synchronous mode where the pacing pulses are delivered in a manner that is dependent upon the intrinsic depolarizations of the heart as sensed by the pacemaker. ICD's must also sense the electrical activity of the heart in order to detect an arrhythmia that will trigger delivery of the shock pulse in an attempt to reverse the condition. Such sensing information can be used to initiate another mode of therapy, and efforts have been made in the past to combine automatic drug delivery by an implantable drug delivery system with either pacemakers, ICD's, or both in order to treat cardiac arrhythmias.

Implantable drug delivery systems suffer from a number of disadvantages, however, when compared with an external drug delivery device. Although the drug reservoir of an implantable delivery device can be replenished, it is difficult to change the drug once it is put into the reservoir, making patient management difficult in cases where a patient's condition either changes or otherwise requires a change of medication. In addition, drugs degrade over time. Finally, there is the risk of leakage from the implanted reservoir, the consequences of which can range from an annoyance to a medical emergency. For these reasons, drug delivery from an external device is preferred in many situations.

In order to control the delivery of drugs or other therapies by an external device, the implanted device must be capable of transmitting command and control information to the external device. This is the primary problem with which the present invention is concerned.

SUMMARY OF THE INVENTION

The present invention relates to a drug delivery system and method in which an implantable medical device communicates with and controls an external drug delivery device with low energy potential signals. The implantable device generates potential signals by operating a current source to cause corresponding electrical potentials that can be sensed at the skin surface by the external drug delivery device. The current source is operated so as to generate a carrier waveform that can be modulated with digitally encoded command information. The external drug delivery device includes electrodes at the skin surface for sensing potentials and circuitry for demodulating the sensed carrier waveform. The drug delivery device may then decode the digital data to extract command information therefrom and deliver a drug accordingly.

In accordance with the invention, the carrier waveform is digitally modulated with the digitally encoded information by varying the amplitude or frequency of the carrier waveform using, for example, amplitude shift-keying or frequency shift-keying. In a particular embodiment, a digital pulse train is modulated with the digitally encoded information by varying the frequency, width, or position of the pulses. The pulse train is then used to amplitude modulate the carrier waveform.

Certain implantable medical devices, such as rate-adaptive pacemakers, may use an impedance technique for measuring minute ventilation and/or cardiac stroke volume. In that technique, an oscillating current is made to flow between two electrodes located within the thorax, and the impedance between the electrodes is measured. In accordance with the invention, the impedance measuring current may be used as the carrier waveform and modulated with digitally encoded information by the implantable device for transmission to the external drug delivery device.

The present invention may be incorporated into a system where the implantable device is a cardiac device such as an implantable cardioverter/defibrillator, cardiac pacemaker, or combination device. A dose of a drug is then delivered by the drug delivery device to a patient upon detection of a particular medical condition such as an arrhythmia. In one embodiment, the drug delivery device is an electrically modulated transdermal drug delivery device designed for external affixation to a patient's skin surface at a suitable location. The electrically modulated transdermal delivery injector may have one electrode with a drug reservoir in contact with the skin, another electrode also contacting the skin, and a voltage source for imposing a voltage between the electrodes. The drug delivery device also has a data communications interface for receiving command signals from the implantable cardiac device, and circuitry for controlling the delivery of the drug in accordance with the command signal.

DESCRIPTION OF A SPECIFIC EMBODIMENT

The present invention is embodied by a drug delivery system in which an implantable medical device capable of sensing a physiological variable or event controls the delivery of a drug from an external delivery device in response to the sensed variable. In the particular embodiment described below in detail, the implantable medical device is a cardiac device such as an implantable cardioverter/defibrillator, pacemaker, or combination device. Among the physiological variables that can be sensed by such a device and used to control the delivery of drugs are heart rhythm, cardiac output, ventilation rate, and myocardial perfusion (i.e., detection of ischemia). When a particular medical condition occurs, such as an arrhythmia or ischemic episode, the cardiac device transmits a command signal to an external drug delivery device that causes the delivery of a specified amount of drug in an attempt to treat the condition. The delivery device preferably delivers the drug transdermally, but alternate embodiments may employ an instrument with circulatory access such as an intravenous line or hypodermic needle.

Command information is transmitted from the implantable device to the drug delivery device via a carrier waveform sensed by the drug delivery device at the skin surface. The command information is encoded digitally and then used to modulate the carrier. The carrier waveform is generated by a means of an oscillating current produced between two electrodes disposed internally and in contact with body fluids. Such a current results in an oscillating dipole electric field that can be sensed externally as the potential difference between two electrodes in contact with the skin. As described below, a preferred embodiment employs as a carrier the same oscillating impedance measuring current used to measure minute ventilation and/or cardiac stroke volume.

The carrier waveform may be modulated with digitally encoded information by a variety of standard modulation techniques such as amplitude shift-keying, frequency shift-keying, phase shift-keying, and M-ary variants of those techniques. Because the impedance between the current injecting electrodes can vary (as, for example, in accordance with cardiac or lung volumes when the electrodes are disposed in a ventricle or elsewhere in the thorax), however, it is preferable to use a modulation technique that is unaffected by changes in the amplitude of the carrier. This is because such impedance variations between the electrodes can affect the potential at the skin surface resulting from a given amplitude of current.

One way to modulate the carrier with the digitally encoded information is to modulate a digital pulse train by varying the frequency, width, or position of the pulses, and then use the modulated pulse train to amplitude modulate the carrier waveform. The pulse train thus constitutes a sub-carrier. In a preferred embodiment, the pulse train is frequency modulated in accordance with the digitally encoded information so that the intervals between successive pulses are interpreted as symbols that signify a particular bit in the case of binary symbols, or a particular bit pattern in the case where more than two symbol states are used (i.e., M-ary modulation methods). In the embodiment described in detail below, the interval between each of the pulses of the pulse train is varied between two values to signify either a 1 or a 0. Each measured pulse interval thus constitutes a binary symbol. Alternate embodiments may employ additional intervals as symbol states in order to increase the data transmission rate. Since a pulse must only be sensed above a certain threshold in order to detect a symbol, this modulation scheme is unaffected by amplitude changes in the modulated carrier.

Figure 1:
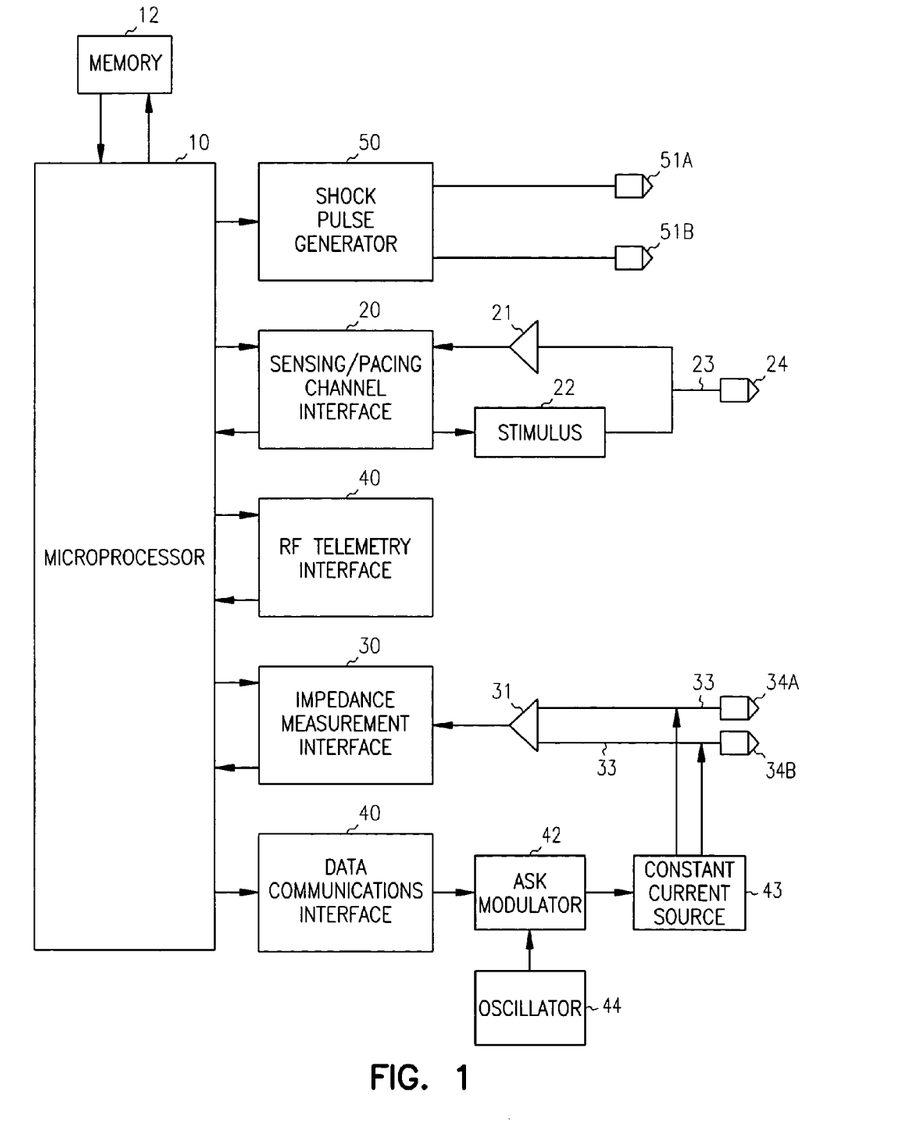
FIG. 1 is a system diagram of an exemplary implantable cardiac device.

FIG. 1 is a system diagram of a microprocessor-based implantable cardioverter/defibrillator with the capability of also delivering pacing therapy. A microprocessor 10 communicates with a memory 12 and peripheral devices via bidirectional address and data busses. The memory 12 typically comprises a ROM or RAM for program storage and a RAM for data storage. The device has atrial and/or ventricular sensing and pacing channels for sensing depolarizations and delivering pacing pulses to the atria and/or ventricle. Each atrial/ventricular sensing and pacing channel comprises an electrode, lead, sensing amplifier, pulse generator, and a channel interface for communicating with the microprocessor 10, represented in the figure by electrode 24, lead 23, sensing amplifier 21, pulse generator 22, and a channel interface 20. A channel interface includes analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. For each channel, the same lead and electrode are used for both sensing and pacing. The sensing channels are used in conjunction with pacing and for detecting arrhythmias. Also interfaced to the microprocessor is a shock pulse generator 50 for delivering cardioversion or defibrillation pulses to the heart via a pair of electrodes 51a and 51b, and a radio frequency telemetry interface 40 for communicating with an external programmer. A battery (not shown) supplies power to the device.

The device also has the capability of measuring the electrical impedance between electrodes 34a and 34b. A current is injected between the electrodes from constant current source 43, and the voltage between the electrodes is sensed and transmitted to the impedance measurement interface 30 through sense amplifier 31. The impedance measurement interface processes the voltage signal to extract the impedance information therefrom and communicates with the microprocessor. Depending upon where the electrodes 34a and 34b are disposed, the impedance measurement can be used to measure minute ventilation or cardiac stroke volume. An example of the latter is described in U.S. Pat. No. 5,190,035, issued to Salo et al., and hereby incorporated by reference.

In order to communicate command information to the external drug delivery device, a current signal is generated between the electrodes 34a and 34b by driving the constant current source 43 with an oscillator 44. The waveform of the oscillator is modulated by an amplitude shift-keying (ASK) modulator 44 in accordance with the output of data communications interface 40. The data communications interface 40 receives digital data from the microprocessor 10 and frequency modulates a digital pulse train such that the interval between successive pulses is a binary symbol. The frequency modulated pulse train is then used as a subcarrier to modulate the carrier waveform. In this embodiment, the same current is used for both impedance measurement and data transmission to the external drug delivery device. Other embodiments may transmit information with current signals that are not also used for impedance measurement, in which case a constant current is not necessary.

Figure 2:
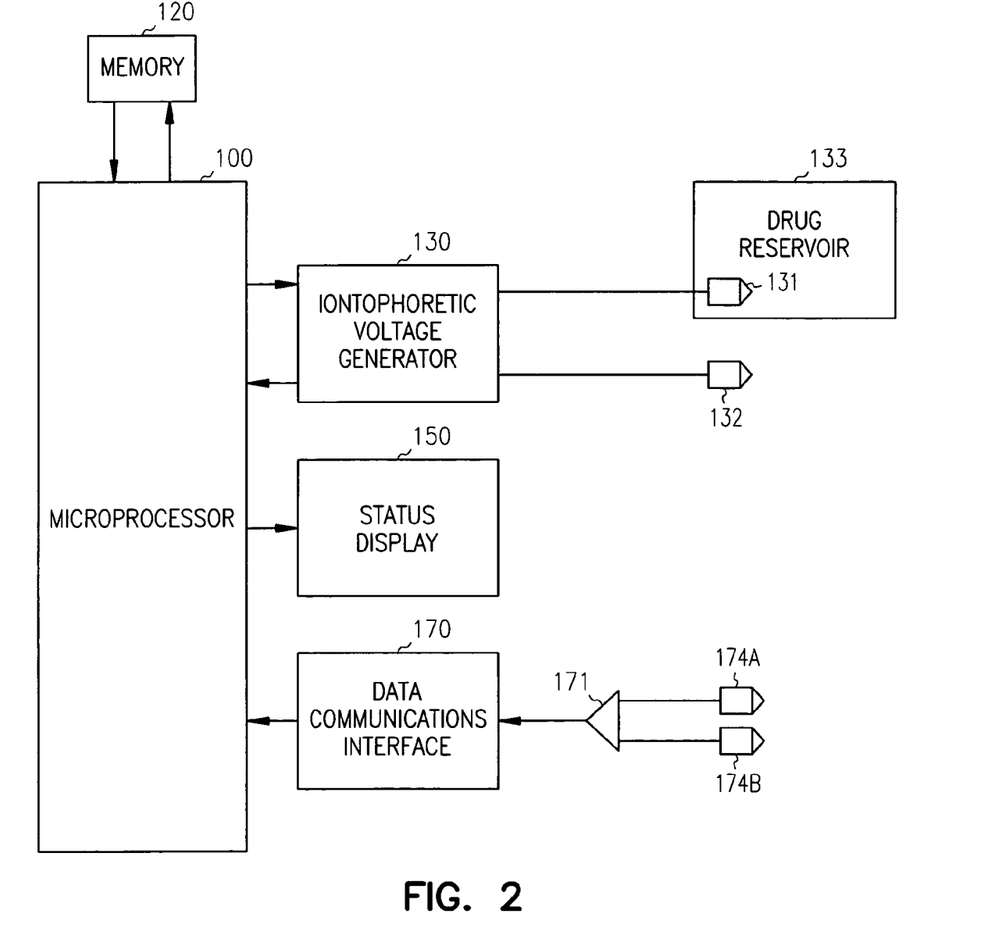
FIG. 2 is system diagram of the drug delivery device.

FIG. 2 is a system diagram of an external drug delivery device for delivering a quantity of a drug in accordance with a command signal received from the implantable cardiac device. The control circuitry of the drug delivery device includes a microprocessor 100 and memory 120. A battery (not shown) supplies power to the device. Interfaced to the microprocessor is a electrically modulated transdermal drug delivery voltage generator 130 for generating a voltage between electrodes 131 and 132. Electrode 131 is electrically connected to a drug reservoir 133 which is adapted for contacting the patient's skin. The term "electrically modulated transdermal drug delivery device" is meant to include any device that uses an electrical field to controllably deliver drugs transdermally such as by e.g., iontophoresis, electroporation, electrorepulsion, or electro-osmosis. Electrode 132 is also adapted for contacting the patient's skin so that when a voltage is impressed across the electrodes, charged drug molecules are caused to migrate from the reservoir 133 through epidermal appendages and pores into the dermal capillary bed where the drug then diffuses into the circulation. The drug may be in the form of an aqueous solution whose pH is adjusted so that most of the drug is in a charged form, with the polarity of the electrodes 131 and 132 adjusted for whether the drug is in anionic or cationic form. The drug solution may then be contained in the reservoir by any medium capable of holding the drug and allowing its free flow when subject to an electrical field such as a gauze patch, or a gel or solution with a porous wrapping. The reservoir 133 is preferably mounted in a frame suitable for affixation to the patient such that the reservoir is in contact with skin. A status display 150 is also interfaced to the microprocessor for displaying information to a user relating to the device's operating status such as battery power remaining, the amount of drug in the reservoir, and a log of previous drug deliveries including the amount of drug delivered.

In order to receive command information from the cardiac device, potentials are sensed at the skin surface between electrodes 174a and 174b by sensing amplifier 171. The output of amplifier 171 is input to data communications interface 170 which demodulates the sensed potentials to derive the digital signal encoded with command information by the cardiac device. The digital signal is then processed by the microprocessor 100 in order to extract the command information contained therein. In this embodiment, the signal transmitted by the cardiac device is a carrier signal ASK modulated with a digital pulse train. The digital pulse train is used as a subcarrier by modulating the frequency of the pulses in accordance with a digital signal encoded with the command information. The time interval between each successive pulse is one of two possible values to indicate a 1 or a 0 and thus constitutes a binary symbol.

Figure 3:
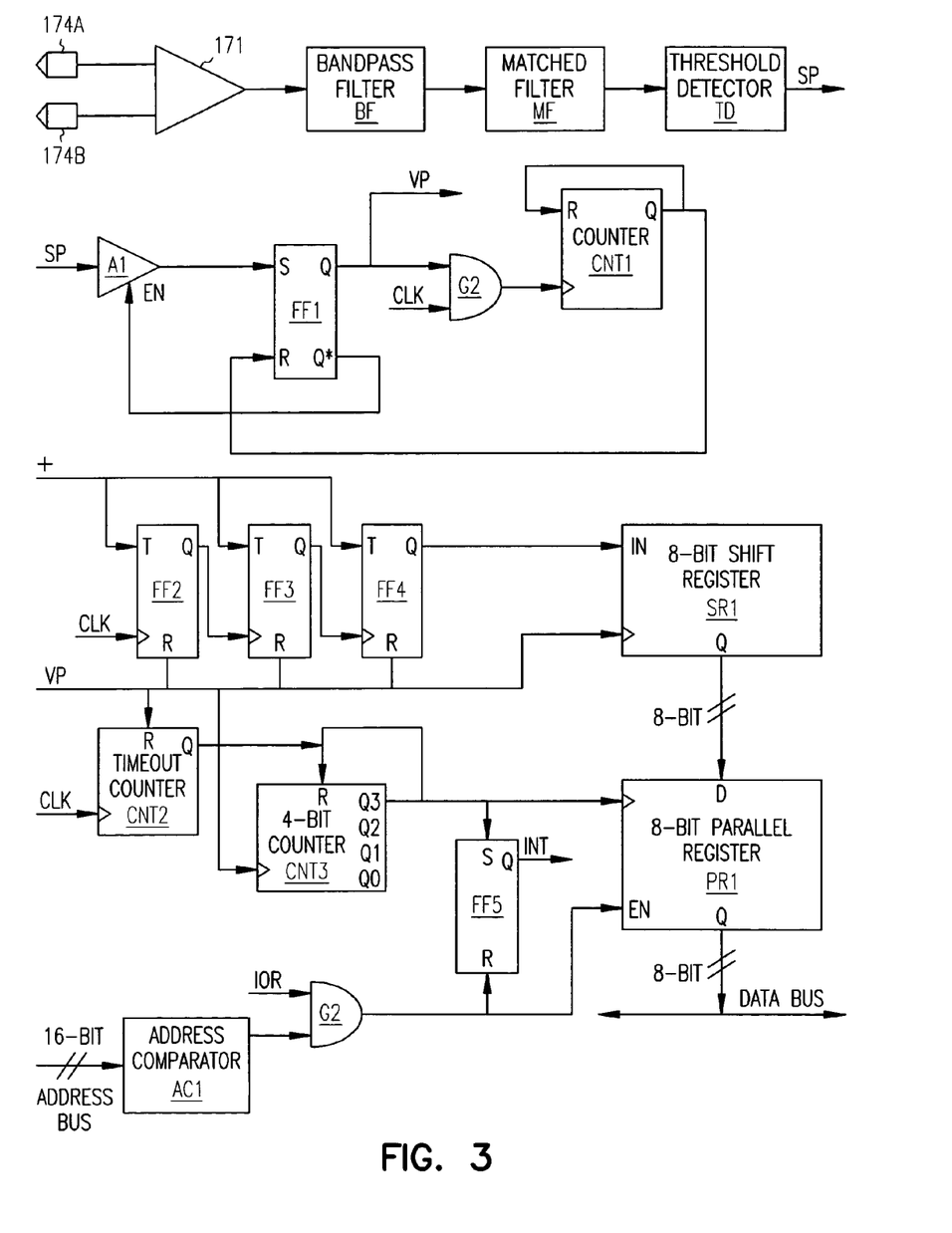
FIG. 3 is a circuit diagram of a data communications interface incorporated into the drug delivery device.

FIG. 3 is a high-level circuit diagram of the data communications interface 170. This particular embodiment uses discrete components to process the sensed potential signals, but the functionality could also be implemented by software executed by the microprocessor 100. The sensed potential signal from amplifier 171 is input to a bandpass filter BF that has its center frequency at the carrier signal frequency. In order to provide further noise immunity, the filtered signal is then input to a matched filter MF. The output of the matched filter MF is essentially a correlation between the sensed signal and a template signal corresponding to a transmitted pulse. The matched filter output is then compared with a specified threshold by threshold detector TD. If the threshold is exceeded, a sensed pulse signal SP compatible with the rest of the digital circuitry is output. The result of these steps is thus the ASK demodulation of the sensed carrier waveform. These operations may be performed by analog components or in the digital domain by processing digitized samples of the sensed signal.

As already noted, the time interval between each transmitted pulse and the preceding transmitted pulse is a symbol indicating either a 0 or a 1. In this embodiment, the interval between each pulse subcarrier pulse train is either T or 2T seconds such that the pulse frequency varies between 1/T and 1/2T Hz. Due to noise, however, the threshold detector TD may output sensed pulse signals separated by a much shorter interval. In order to avoid such spurious signals, only one sensed pulse SP within a specified limit time period is allowed to be regarded as a valid pulse and used to determine the interval symbol. A sensed pulse signal SP is input to a buffer A1 which either passes the signal or not in accordance with its tri-state enable input EN. If buffer A1 is enabled, the SP signal is passed to the set input S of flip-flop FF1. The Q output of FF1 is then asserted as a valid pulse signal VP which is decoded as a 1 or 0 by other circuitry using only the rising edge of VP. VP is maintained high for the limit time period until flip-flop FF1 is reset by the output of counter CNT1. When VP is asserted, AND gate G1 passes clock pulses CLK to the clock input of counter CNT1. When counter CNT1 has counted a number of clock pulses equal to the specified limit time period, the Q output of the counter corresponding to the limit time period is asserted which then resets flip-flop FF1 and the counter itself. Resetting of flip-flop FF1 deasserts the valid pulse signal VP which disables further clocking of counter CNT1 through gate G1 and readies the flip-flop for receipt of another sensed pulse signal SP. In order to ensure that VP is deasserted after timeout of the counter CNT1 so that another rising edge of VP can be output, the complementary output Q* of FF1 is used to tri-state disable the buffer A1 and prevent the setting of flip-flop FF1 until the flip-flop is reset by the Q output of counter CNT1. The rising edges of the signal VP thus correspond to the pulse train subcarrier which has been modulated with the digitally encoded command information.

In order to demodulate the subcarrier, the rising edge of each asserted VP signal is used to detect a transmitted symbol in accordance with whether the time interval elapsed since the previous assertion of VP is T or 2T. In this embodiment, the period of the CLK signal is assumed to be 3T/8 so that the clock frequency is 8/3 times as fast as the fastest symbol rate 1/T of the transmitted signal. Flip-flops FF2, FF3, and FF4 are T-type flip-flops which together make up a divide-by-8 ripple counter clocked by the CLK signal so that the Q output of FF4 is a square wave of period 3T. The ripple counter is reset by each assertion of VP so that the Q output of FF4 transitions from low to high at a time 3T/2 after VP is asserted. This allows the next assertion of VP to use the output of the ripple counter as a data signal corresponding to the interval since the previous assertion of VP. That data signal is then clocked into a shift register SR1. A 0 is clocked into SR1 if the VP signal occurs earlier than time 3T/2 since the previous VP assertion, and a 1 is clocked in if the VP occurs between a time 3T/2 and 3T after the previous VP assertion when the ripple counter output is high. The time 3T/2 thus represents the mid-point between the two interval symbol states T and 2T. In this way, each VP pulse results in a 1 or a 0 being clocked into the shift register SR1 in accordance with the time interval since the previous VP pulse. Note that if no previous VP pulse has been received, the first VP pulse clocks an indeterminate value into the shift register and should be disregarded.

Shift register SR1 is an 8-bit register so that the register is full after eight VP assertions, and the data contained therein must to transferred elsewhere. Counter CNT3 is a 4-bit counter clocked by the rising edge of VP so that its most significant bit output $Q_3$ is asserted after eight assertions of VP. $Q_3$ is tied to the clock input of 8-bit parallel register PR1 so that its assertion loads the 8-bit output of shift register SR1 into register PR1. Assertion of $Q_3$ also resets the counter CNT3. In this manner, the demodulated data contained in shift register SR1 is transferred to register PR1 after every eight assertions of VP. A timeout counter CNT2 is also clocked by CLK with its Q output corresponding to a specified timeout period used to reset counter CNT3. Thus, in the event that no VP assertion is received after the specified timeout period, the framing of data into 8-bit bytes is restarted with the next VP pulse.

Assertion of $Q_3$ also sets flip-flop FF5 which causes assertion of an interrupt signal INT to the microprocessor signifying that the data contained in register PR1 is available for reading. The interrupt servicing routine then accesses the register PR1 by putting its address on the address bus which causes the output of address comparator AC1 to go high. AND gate G2 then passes the assertion of a read strobe IOR to enable the tristate outputs of register PR1 and puts its 8-bit contents onto the data bus. The read strobe IOR also resets the flip-flop FF5 to clear the interrupt signal.

Data is thus received by the microprocessor in the form of consecutive 8-bit bytes. Such data can include error-correcting codes in order for the microprocessor to determine whether the data should be regarded as valid command information. The cardiac device may repeat each transmission a specified number of times in order to increase the probability that a valid transmission is received. The data can be segregated into separate frames for this purpose with the beginning and end of each frame signified by particular data bytes.

In operation, the cardiac device detects a particular medical condition such as an arrhythmia by an analysis of the digitized information received from the sensing channels according to algorithms implemented by the programmed microprocessor 10. Upon detection of a particular condition indicating the need for drug delivery, a command signal is generated which consists of a coded message suitable for transmission via the data communications interface 40. The command signal is then used to modulate the carrier signal generated by the current source 43 which is received by the drug delivery device. Upon sensing of the transmitted current signal at the skin surface and demodulation to derive the command signal, the transdermal drug delivery voltage generator 130 is activated by the microprocessor 100 to deliver a quantity of the drug to the patient. The command signal can also contain information relating to the amount of drug that is to be delivered by the drug delivery device and/or the time period over which the delivery is to take place.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A drug delivery system, comprising:
   an implantable medical device that includes two electrodes adapted for disposition at an internal body location in contact with body fluids, a current source for injecting current between the two electrodes, an oscillator for driving the current source, and circuitry for modulating the waveform produced by the oscillator to produce potential signals encoded with command information that can be sensed at a skin surface location; and,
   an external drug delivery device for affixation to a patient having incorporated therein a data communications interface for demodulating potential signals sensed at a skin surface location, circuitry for deriving command information from the demodulated potential signals, and circuitry for controlling delivery of a drug in accordance with the command information.

2. The system of claim 1, wherein the potential signals are transmitted in the form of a carrier waveform digitally modulated with the digitally encoded command information by varying the amplitude of the carrier waveform.

3. The system of claim 1, wherein the potential signals are transmitted in the form of a carrier waveform digitally modulated with the digitally encoded command information by varying the frequency of the carrier waveform.

4. The system of claim 1, wherein the potential signals are transmitted in the form of a digital pulse train modulated with the digitally encoded information by varying the frequency of the pulses and amplitude modulating a carrier waveform with the modulated pulse train.

5. The system of claim 1, wherein the potential signals are transmitted in the form of a digital pulse train modulated with the digitally encoded information by varying the width of the pulses and amplitude modulating a carrier waveform with the modulated pulse train.

6. The system of claim 1, wherein the potential signals are transmitted in the form of a digital pulse train modulated with the digitally encoded information by varying the position of the pulses and amplitude modulating a carrier waveform with the modulated pulse train.

7. The system of claim 1, wherein the implantable medical device is a cardiac device comprising a sensing channel for sensing electrical activity occurring in a patient's heart and generating sensing signals in accordance therewith, circuitry for extracting information from the sensing signals, and circuitry for detecting a particular medical condition from the extracted information and generating a command signal to the external drug delivery device if the medical condition is present.

8. The system of claim 7, wherein the cardiac device sends a command signal upon detection of a cardiac arrhythmia.

9. The system of claim 1, wherein the implantable medical device further comprises circuitry for performing an impedance measurement related to a physiological variable by sensing the voltage between the two electrodes as current is injected from the current source.

10. The system of claim 1, wherein the drug delivery device is an electrically modulated transdermal injector comprising:
   a first electrode connected to a first drug reservoir for containing a drug and contacting a patient's skin;
   a second electrode for contacting a patient's skin; and,
   a controllable power source for connecting to the electrodes and imposing a voltage therebetween.

* * * * *

UNITED STATES PATENT AND TRADEMARK OFFICE
CERTIFICATE OF CORRECTION

PATENT NO.        : 7,425,210 B2
APPLICATION NO. : 10/743507
DATED             : September 16, 2008
INVENTOR(S)       : Sweeney et al.

Page 1 of 1

It is certified that error appears in the above-identified patent and that said Letters Patent is hereby corrected as shown below:

On the face page, in field (56), under "U.S. Patent Documents", in column 1, line 1, delete "Elinwood, Jr." and insert -- Ellinwood, Jr. --, therefor.

Signed and Sealed this

Third Day of November, 2009

David J. Kappos
*Director of the United States Patent and Trademark Office*